United States Patent [19]

Plass

[11] Patent Number: 5,503,625
[45] Date of Patent: Apr. 2, 1996

[54] KIT FOR ADMINISTERING RADIOLOGIC MATERIAL TO AN OSTOMATE AND METHOD OF USE

[75] Inventor: Ronald A. Plass, Haywards Heath, England

[73] Assignee: E. R. Squibb & Sons, Inc., Princeton, N.J.

[21] Appl. No.: 332,604

[22] Filed: Oct. 31, 1994

Related U.S. Application Data

[63] Continuation of Ser. No. 924,780, Aug. 4, 1992, abandoned.

[30]  Foreign Application Priority Data

Sep. 4, 1991 [GB] United Kingdom ............... 9118852

[51] Int. Cl.$^6$ ........................................................ A61M 1/00
[52] U.S. Cl. .................. 604/317; 604/305; 604/336; 604/337; 128/887
[58] Field of Search ................................. 604/305, 317, 604/322, 326, 327, 332, 336, 337, 338, 339, 355, 263, 271, 283, 285, 20, 21; 606/191; 128/887, 888

[56]  References Cited

U.S. PATENT DOCUMENTS

| | | | |
|---|---|---|---|
| 4,360,025 | 11/1982 | Edwards | 604/336 |
| 4,778,446 | 10/1988 | Jensen | 604/317 |
| 4,778,456 | 10/1988 | Lokken | 604/305 |
| 4,941,869 | 7/1990 | D'Amico | 604/337 |
| 5,045,052 | 9/1991 | Sans | 604/337 |
| 5,045,056 | 9/1991 | Behl | 604/49 |
| 5,054,497 | 10/1991 | Kapp et al. | 128/887 |
| 5,125,916 | 6/1992 | Panebianco et al. | 604/332 |

FOREIGN PATENT DOCUMENTS

| 2431888 | 1/1976 | Germany | 128/887 |

*Primary Examiner*—Paul B. Prebilic
*Attorney, Agent, or Firm*—Stuart E. Krieger

[57]  ABSTRACT

A radiology kit for use with a catheter includes a first connection member 20 for attachment to the skin of the patient around the stomal orifice and a second connection member 30 (a cap) constructed for releasable attachment to a first connection means, i.e. a rib 23, on the first connection member. The cap has an end wall 33 with a hole 39 therein through which a catheter 40 can be threaded. A third connection member 50 of the kit is attached to a drainage sleeve 52 and constructed for releasable attachment to a second connection means, i.e. a rib 25 on the first connection member 20.

10 Claims, 4 Drawing Sheets

1

KIT FOR ADMINISTERING RADIOLOGIC MATERIAL TO AN OSTOMATE AND METHOD OF USE

This is a continuation of application Ser. No. 07/924,780, filed Aug. 4, 1992, now abandoned.

BACKGROUND OF THE INVENTION

This invention relates to a kit for use in radiology, and to some of the components for such a kit. In some radiology operations, it is required to introduce a radioactive tracer liquid into a patient's intestine using a catheter. Such a patient may have a surgically-created stoma and the catheter may need to extend directly into the stoma. Currently it is necessary for the catheter to be held in position either manually by the patient, or by fixing the catheter to the skin with adhesive tape. The former method is unsatisfactory because it places a requirement on the patient which not all patients may be able to fulfil and the second method is unsatisfactory because the adhesive tape and consequently the catheter may become dislodged, or an unintended movement of the catheter (which is unlikely to be satisfactorily restrained by the tape) may cause discomfort or injury to the patient.

It would be desirable if there were available a radiology kit which overcomes or reduces these quite serious problems.

OBJECTS AND SUMMARY OF THE INVENTION

According to one aspect of the present invention, there is provided a radiology kit for use with a catheter, the kit comprising a first connection member for attachment to the skin of the patient around the stomal orifice, a second connection member constructed for releasable attachment to a first connection means on the first connection member and having a cap-like formation with a hole therein through which a catheter can be threaded, and a third connection member attached to a drainage sleeve and constructed for releasable attachment to a second connection means on the first connection member.

According to another aspect of the present invention, there is provided a method of using such a kit, comprising the steps of:

(a) fixing the first connection member to the patient;
(b) threading a catheter through a hole in an end wall of the second connection member;
(c) checking the condition and placement of the catheter by inflation of a balloon section of the catheter within the second connection member, and then deflating;
(d) placing the catheter free end into or towards the stoma an appropriate distance so that the balloon section is either just within or just outside the protruding end of the stoma;
(e) fitting the second connection member onto the first connection means of the first connection member;
(f) inflating the catheter balloon either gently inside the stoma or within the second connection member, so sealing off the stoma;
(g) feeding required radioactive liquid (e.g. from syringe) via the catheter into the stoma;
(h) fitting the third connection member onto the second connection means of the first connection member, having fed the catheter through the open top of the drainage sleeve; and
(i) when the appropriate radioactive evaluation is complete, separating the second connection member from the first, allowing it to remain on the catheter and within the sleeve, and permitting fluid to drain from the stoma into the sleeve.

Preferably the first connection member comprises a medical grade adhesive pad secured to an annular flange having extending therefrom, away from the pad, a pair of upstanding ribs of closed loop form. Each such rib is preferably circular, and extends substantially perpendicularly away from the flange and has an external rim formation and an internally located flexible deflectable sealing strip formation. These inner and outer ring formations constitute respective first and second connection means. Preferably the second connection member comprises a cap-like or cup-like formation having a cover with a central hole through which a catheter can be threaded and an annular flange which is provided with a channel formation designed for co-operation in snap-fit manner with the first connection means of the first connection member. The hole through the cover may be made by two or more crossed slits so as to accommodate catheters of different outside diameters. The cap may be constructed from plastics material having an accordion-like stepped formation to allow the interior volume of the cap-like second connection member to be varied. Preferably the third connection member comprises a member of closed loop form, preferably annular, which is channel-shaped in cross-section and which is constructed for snap-fit engagement and disengagement with the second connection means on the first connection member. Attached to the third connection member is a drainage sleeve. This may be provided with a pressure snap-fit closure or zip type closure across its top edge whereby the normally open top end of the drainage sleeve can be sealed closed when desired. The drainage sleeve may if desired have a closure clip at its normally open bottom end.

DESCRIPTION OF THE DRAWINGS

In the accompanying drawings:

The invention will be better understood from the accompanying drawings in which FIGS. 1–8 illustrate an embodiment of the invention and show stages in its use.

FIG. 1 shows a pad 12 of medical-grade adhesive material, (e.g. that sold by ConvaTec Limited under the Registered Trade Mark "STOMAHESIVE) and 14 is a removable film or sheet e.g. of release paper. Attached to the front surface of the pad 12 is a first connection member 20. The first connection member 20 preferably takes the form of a substantially flat annular flange having a central hole and having first and second connection means on its surface opposite to that by which it is secured to the pad 12. The preferred first and second connection means are annular ribs 23 and 25. Each of these may be provided with an integral deflectible seal strip extending fully around the rib. The seal strip may be internal or external of the respective rib. Each of the ribs is constructed for snap-fit engagement with a respective channel, one such channel being on the second and one on the third connection means.

FIGS. 3 and 4 illustrate a second connection member 30 which is of cup-like form with an end or base wall 33 (FIGS. 5 and 7). It also has a flange 32 from which projects two ribs 34, 36 together defining a channel into which a cooperating rib 23 on the first connection member 20 can be snap-fitted. The member 30 has a central hole 39 in its end wall 33 to receive a catheter 40.

In FIG. 2 the pad 12 is seen applied to the peristomal area of a wearer whose stoma 13 projects through a central hole in the pad 12. The member 20 also has a central hole 21.

In FIG. 4 the member 30 is seen with a balloon catheter 40 pushed through the hole 39, the catheter balloon 42 being inflated.

The preferred and recommended manner of use of the parts described and illustrated is as follows.

Figure 5:
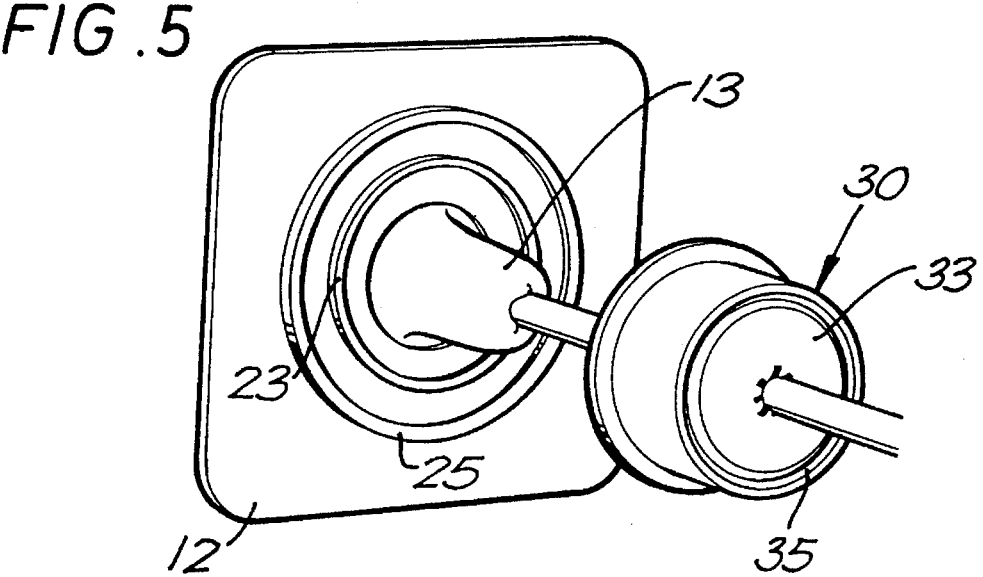
FIG. 5 is a perspective view of a cap, catheter and pad according to the present invention.

First the release paper 14 is peeled off and the medical grade adhesive pad 12 is attached to the peristomal region of the patient in the same way as would be done with the widely known and conventional Squibb-ConvaTec System II/IV ostomy coupling. The catheter 40, for example a Foley 12-22 French gauge catheter is inserted through the hole 39 in the end wall or cap portion (33, FIG. 5) of the second connection member 30. The second connection member 30 may advantageously have slits extending radially outwardly from this hole so that catheters of a variety of outside diameters can readily be pushed through it. The second connection member also has its end wall 33 connected to a cylindrical wall portion thereof by a series of accordion like rings 35, FIG. 5, giving a foldable or bellows structure, so that by pushing the wall 33 inwardly or outwardly it can take up different positions by virtue of the accordion ring arrangement, so providing a different internal volume within the second connection member 30. The nurse or paramedical assistant or surgeon adjusts the projecting length of catheter 40 as desired and when appropriate introduces the free end of the catheter into the stoma 13. The second connection member 30 is then snapped into engagement with the first connection means 23 on the first connection member 20.

Figure 1:
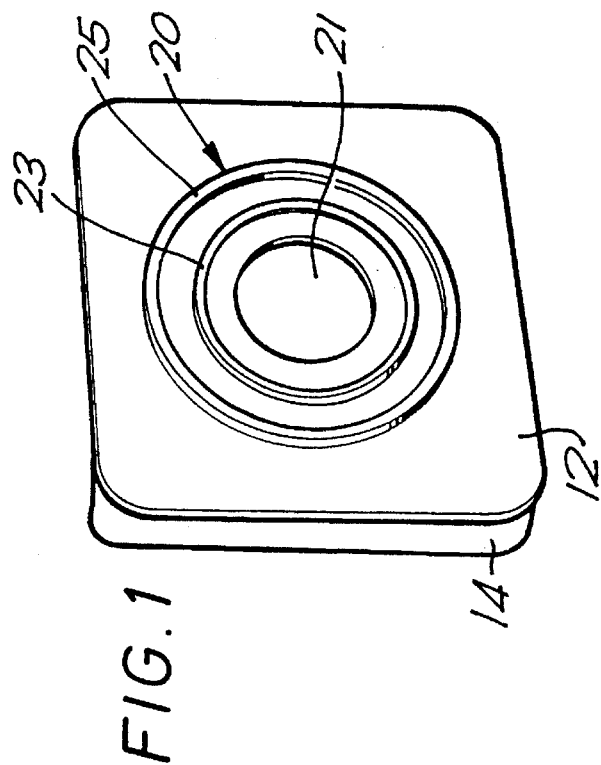
FIG. 1 is a perspective view of a pad which is part of a radiologic kit according to the present invention.
Figure 2:
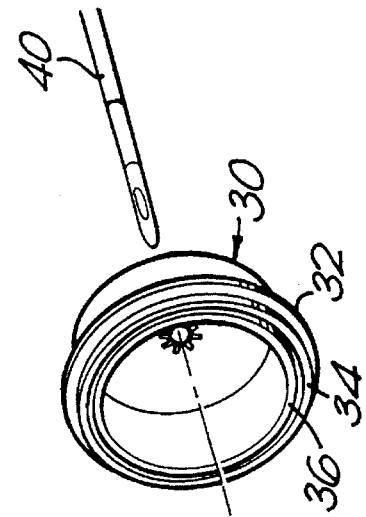
FIG. 2 is a perspective view of a radiologic kit composed of a pad, cap and catheter according to the present invention.
Figure 2:
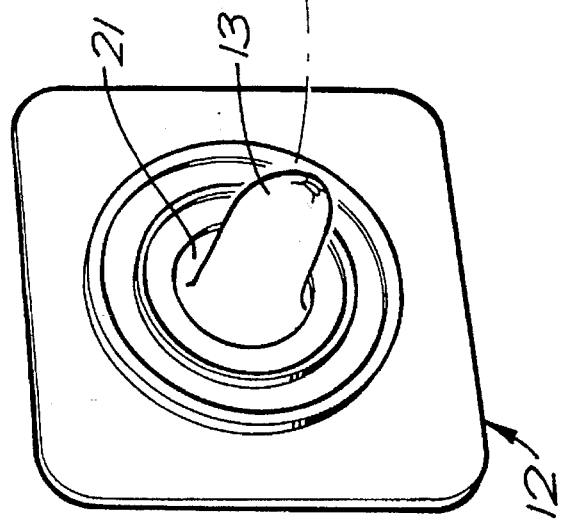
Figure 3:
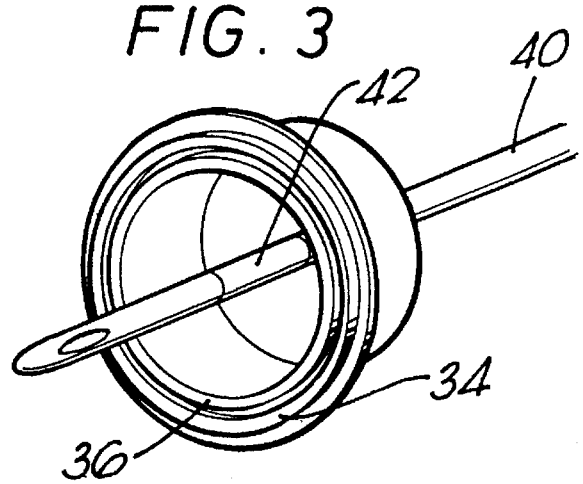
FIG. 3 is a perspective view of a deflated balloon catheter and cap according to the present invention.
Figure 4:
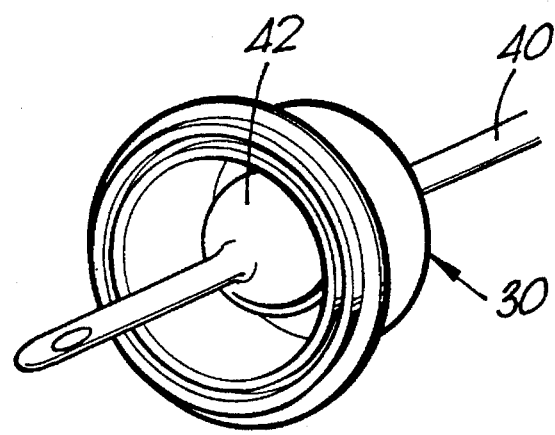
FIG. 4 is a perspective view of an inflated balloon catheter and cap according to the present invention.
Figure 8:
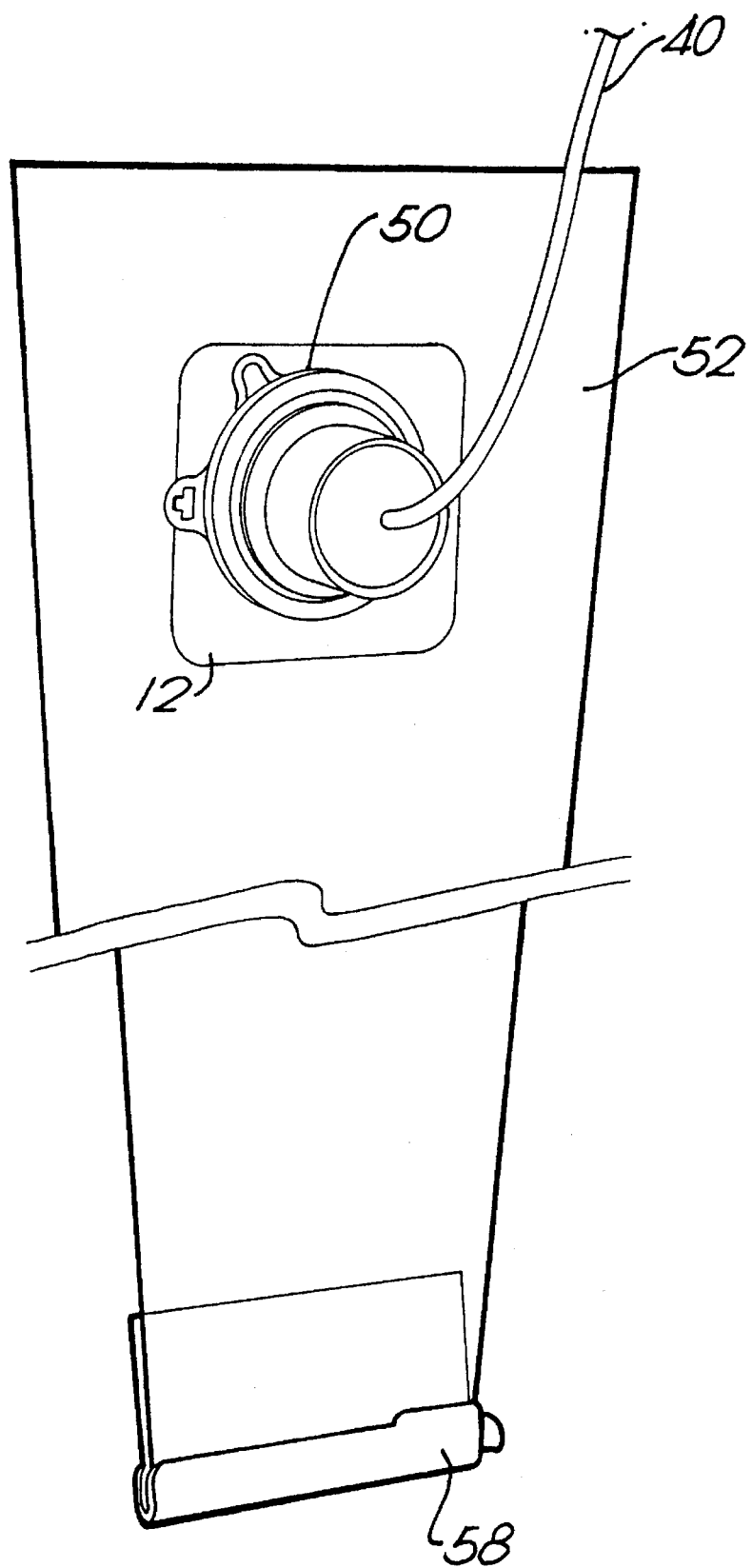
FIG. 8 is a perspective view of an assembled kit including a pad, cap, catheter and drainage sleeve in accordance with the present invention.

Prior to this step the catheter has been threaded through the open top of a drainage sleeve 52, FIG. 8, and out of the sleeve through a central hole in an annular third connection member 50. The third connection member 50 is then snap-fitted, by gentle pressure, to the second connection means 25 of the first connection member 20. This having been accomplished, then assuming that a catheter having an inflation balloon is being used, as will normally be the case, the balloon is then inflated by providing inflation fluid in a conventional manner, and the inflation is continued until the catheter is firmly held within the second connection member (as seen in FIG. 4) with the catheter balloon walls in contact with the stoma and with the interior wall of the second connection member 30. The inflated balloon 42 of the catheter 40 bears against the stoma with steady but gentle pressure and reliably holds the catheter within the second connection member. The balloon 42 therefore serves to provide a seal between the second connection member 30 and the stoma 13 of the patient. However, providing the balloon is not over inflated, the patient experiences no pain but merely feels a comfortable security as regards the placement of the catheter.

In an alternative manner of use, the catheter end is pushed into the stoma until the balloon region 42 is located just within the stoma. Then the balloon is inflated gently within the stoma.

Infusion of the radioactive solution can then proceed in the manner described later.

Figure 6:
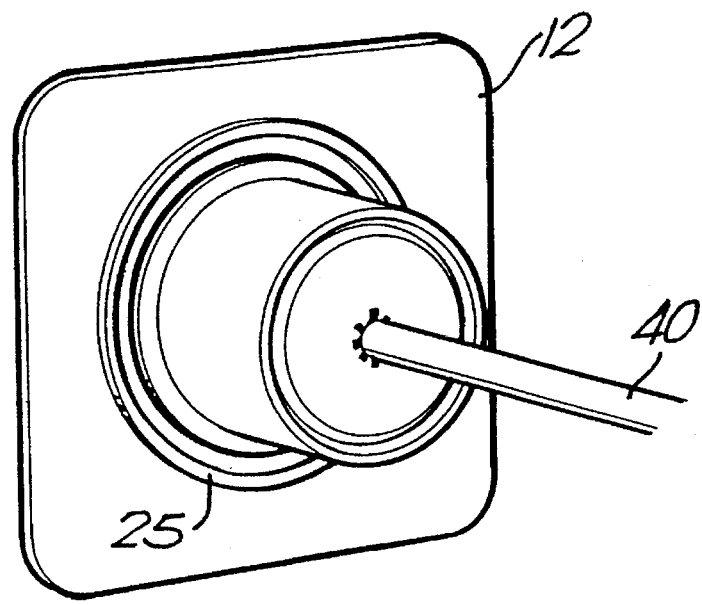
FIG. 6 is a perspective view of an assembled radiologic kit including a pad, extendable cap and deflated balloon catheter in accordance with the present invention.
Figure 7:
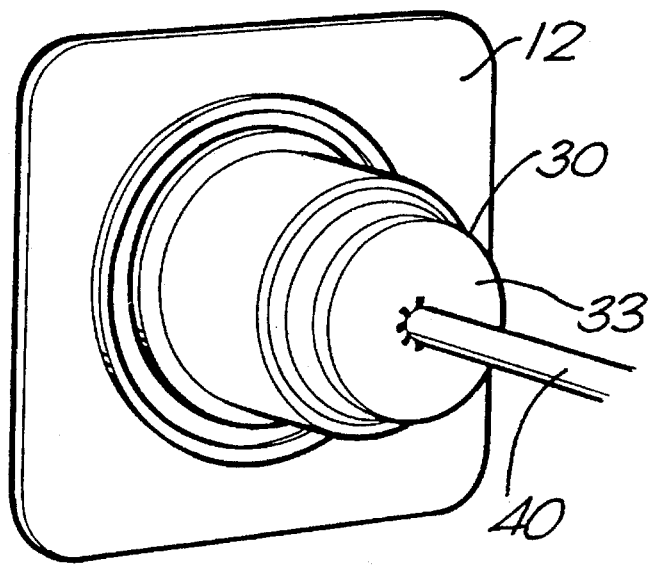
FIG. 7 is a perspective view of an assembled radiologic kit including a pad, extendable cap and inflated balloon catheter in accordance with the present invention.

FIG. 6 shows the second connection member (or cup) 30 being snap-fitted to the first connection member 20 secured to the pad 12; and FIG. 7 shows these fitted together while the catheter balloon is being inflated within the cup 30, causing a bulging of the end wall 33 of the cup.

The drainage or irrigation sleeve 52, which has thereon the third connection member 50 is shown in FIG. 8 snap-fitted to the outer rib 25 on the first connection member 20, the catheter being fed through the opening in the top of the sleeve 52. A suitable clip 58 closes the otherwise open bottom end of the sleeve 52.

A barium solution, or other radioactive solution as desired, is fed into the patient via the catheter. The catheter is then closed off while any X-ray plates are taken or other measurement of radioactive emanation is carried out. Then, if desired, fluid may be withdrawn from the patient's body through the catheter or alternatively the catheter balloon 42 may be allowed to deflate and the second connection member 30 removed from the first connection member 20. Any discharge leaving the stoma passes through the third connection member 50 and into the drainage sleeve 52. Of course during this stage, the top closure (which may be a zip or press-fit plastics rib and groove arrangement) would be closed. The second connection 30 member may be allowed to remain on the end of the catheter but loose within the top portion of the sleeve while any discharge from the stoma drains into the drainage sleeve 52.

At the end of the irrigation cycle, the second connection member 30 is detached from the rib 23 of the first connection member 20, and the catheter with the member 20 thereon may be withdrawn from the open top of the sleeve while any discharge from the patient exits via the sleeve 52 into a suitable receptacle.

In an alternative method of procedure, the catheter end may be left within the stoma and any discharge from the stoma allowed to drain out through the catheter.

After full drainage of barium or other substance from the patient, the third connection member and drainage sleeve attached to it may be removed, and a conventional ostomy bag immediately fixed (i.e. snap-fitted) onto the first or second connection means of the first connection member, according to the size of the coupling member on the ostomy bag.

It will be seen that the kit specifically described and illustrated above completely avoids the patient having to hold the catheter in position. This is of course important because many elderly patients are unable to hold a catheter firmly for any length of time, and the obligation to do so is stress-inducing. In addition, the kit permits a clean and safely enclosed procedure of draining the barium from the patient. According to prior conventional procedures, it was extremely hard to avoid all spillage of barium or other radioactive liquids. To the best of Applicant's knowledge and belief, this kit is the first one wherein spillage of radioactive barium can be consistently avoided; in the use of the present invention the barium or other radioactive liquid is constrained to exit into the drainage sleeve. This is a considerable advantage in that barium spillage is a safety hazard and because "cleaning down" after barium spillage normally involves hospital nurses or others in considerable work which undesirably deflects them from professional duties. Moreover, while application of barium liquid for radiology will seldom be a welcome occurrence for a patient, by the use of the kit described and illustrated herein, increased comfort and security for the patient can be provided.

I claim:

1. A radiology kit for use on a patient having a stomal orifice, the kit comprising:

a pad having an opening extending therethrough, said pad having a first surface with adhesive for securing said pad to the patient with said opening and stomal orifice of said patient directly aligned, said pad having a second surface opposing said first surface, said second surface including first attachment means for attaching a member to said pad; and a cover member for covering said opening and stomal orifice, said cover member having second attachment means for attaching said cover member to said first attachment means, said cover member including a passageway predeterminedly sized for receiving a catheter therethrough;

a catheter predeterminedly dimensioned so as to extend through said passageway and into the stomal orifice for dispensing radiologic material through said catheter into said patient through the stomal orifice; and a source of radiologic material attachable to said catheter.

2. The radiology kit of claim 1 wherein said catheter includes an inflatable balloon portion, said balloon portion being capable of insertion into said stomal orifice and being inflatable so as to close off the stomal orifice.

3. The radiology kit of claim 1 wherein said catheter includes an inflatable balloon portion capable of insertion within said cover member and being inflatable so as to close off the stomal orifice.

4. The radiology kit of claim 1 further comprising a drainage sleeve attachable to said first attachment means for receiving material outletting from said stomal orifice.

5. The radiology kit of claim 1 wherein said adhesive on said pad is a medical grade adhesive, said first attachment means includes an upstanding rib formation, and said second attachment means of said cover member has a channel that snap fits with said rib formation.

6. The radiology kit of claim 1 wherein said first attachment means includes a projecting rib and said second attachment means includes a channel into which said rib is secured.

7. The radiology kit of claim 1 wherein said second attachment means includes a projecting rib and said first attachment means includes a channel into which said rib is secured.

8. The radiology kit of claim 1 wherein said first attachment means includes a first connecting member for connecting to a second connecting member, and further comprising a drainage sleeve having an inlet opening, said drainage sleeve having a second connecting member for connecting to said first connecting member and attaching said drainage sleeve to said pad with said inlet opening aligned with said pad opening and stomal orifice for receiving material outletting said stomal orifice.

9. The radiology kit of claim 8 wherein said first connecting member is a projecting rib and said second connecting member is a channel into which said rib is secured.

10. The radiology kit of claim 9 wherein said second connecting member is a projection rib and said first connecting member is a channel into which said rib is secured.

\* \* \* \* \*